United States Patent
Peterson et al.

(10) Patent No.: US 12,318,172 B2
(45) Date of Patent: *Jun. 3, 2025

(54) ELECTROCARDIOGRAM-BASED ESTIMATION OF ECHOCARDIOGRAPHY PARAMETERS

(71) Applicant: HeartSciences Inc., Southlake, TX (US)

(72) Inventors: Aaron Peterson, Coppell, TX (US); Partho Sengupta, Metuchen, NJ (US); David Krubsack, Onalaska, WI (US)

(73) Assignee: HEARTSCIENCES INC., Southlake, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/818,209

(22) Filed: Aug. 8, 2022

(65) Prior Publication Data

US 2022/0378305 A1 Dec. 1, 2022

Related U.S. Application Data

(63) Continuation of application No. 16/948,021, filed on Aug. 27, 2020, now Pat. No. 11,445,918.

(Continued)

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/0285* (2013.01); *A61B 5/316* (2021.01);
(Continued)

(58) Field of Classification Search
CPC ..... A61B 5/02028; A61B 5/349; A61B 5/339; A61B 5/316; A61B 5/0285; A61B 5/7267; G16H 50/30; G06N 3/08
See application file for complete search history.

(56) References Cited

U.S. PATENT DOCUMENTS

| | | | |
|---|---|---|---|
| 2014/0107510 A1* | 4/2014 | Bogun | A61B 5/316 600/523 |
| 2017/0086693 A1 | 3/2017 | Peterson et al. | |

(Continued)

FOREIGN PATENT DOCUMENTS

| WO | WO-2019057676 A1 | 3/2019 |
|---|---|---|
| WO | WO-2019070978 A1 | 4/2019 |

OTHER PUBLICATIONS

"U.S. Appl. No. 16/948,021, Non Final Office Action mailed Mar. 18, 2022", 7 pgs.

(Continued)

*Primary Examiner* — Jon Eric C Morales
(74) *Attorney, Agent, or Firm* — SCHWEGMAN LUNDBERG & WOESSNER, P.A.

(57) ABSTRACT

Machine-learned computational models can be trained to estimate echocardiogram parameters (as conventionally measured by echocardiography) from electrocardiograms and/or electrocardiogram-derived time-domain and/or time-frequency features. In some embodiments, a multi-level model architecture includes a level to derive the echocardiogram parameter estimate(s), with input features to that level being computed in a preceding level, and/or with one or more echocardiogram parameter estimate(s) flowing into a subsequent layer to compute downstream qualitative or quantitative indicators of heart function.

29 Claims, 9 Drawing Sheets

Related U.S. Application Data

(60) Provisional application No. 63/065,837, filed on Aug. 14, 2020, provisional application No. 62/894,598, filed on Aug. 30, 2019.

(51) Int. Cl.
  *A61B 5/0285* (2006.01)
  *A61B 5/316* (2021.01)
  *A61B 5/339* (2021.01)
  *A61B 5/349* (2021.01)
  *G06N 3/08* (2023.01)
  *G16H 50/30* (2018.01)

(52) U.S. Cl.
  CPC .............. *A61B 5/339* (2021.01); *A61B 5/349* (2021.01); *A61B 5/7267* (2013.01); *G06N 3/08* (2013.01); *G16H 50/30* (2018.01)

(56) References Cited

U.S. PATENT DOCUMENTS

| | | | | |
|---|---|---|---|---|
| 2017/0091567 | A1* | 3/2017 | Wang | A61B 5/349 |
| 2017/0196473 | A1* | 7/2017 | Krubsack | A61B 5/316 |
| 2019/0076044 | A1 | 3/2019 | Krubsack et al. | |
| 2021/0059540 | A1 | 3/2021 | Peterson et al. | |

OTHER PUBLICATIONS

"U.S. Appl. No. 16/948,021, Non Final Office Action mailed Aug. 19, 2021", 8 pgs.

"U.S. Appl. No. 16/948,021, Notice of Allowance mailed Jul. 14, 2022", 7 pgs.

"U.S. Appl. No. 16/948,021, Response filed Nov. 19, 2021 to Non Final Office Action mailed Aug. 19, 2021", 8 pgs.

"European Application Serial No. 20193719.0, Extended European Search Report mailed Dec. 7, 2020", 9 pgs.

"European Application Serial No. 20193719.0, Response filled Dec. 14, 2021 to Extended European Search Report mailed Dec. 7, 2020", 33 pgs.

Kagiyama, Nobuyuki, et al., "Artificial Intelligence: Practical Primer for Clinical Research in Cardiovascular Disease", DOI: 10.1161/JAHA.119.012788, (Aug. 27, 2019), 12 pages.

Nobuyuki, Kagiyama, et al., "Machine Learning Assessment of Left Ventricular Diastolic Function Based on Electrocardiographic Features", Journal of the American College of Cardiology, vol. 76, No. 8, (Aug. 17, 2020), 930-941.

Sengupta, Partho P, et al., "Prediction of Abnormal Myocardial Relaxation From Signal Processed Surface ECG", Journal of the American College of Cardiology, vol. 71, No. 15, (Apr. 9, 2018), 1650-1660.

Sengupta, Partho P, et al., "Supplementary Table 1. Comparison of the performance of various machine learning classifiers", Journal of the American College of Cardiology, vol. 71, No. 15, [Online] Retrieved from the Internet: <URL: https://ars.els-cdn.com/content/image/1-s2.0-S073510971833256X-mmc1.pdf>, (Apr. 9, 2018), 11 pgs.

Tison, Geoffrey H, et al., "Automated and Interpretable Patient ECG Profiles for Disease Detection, Tracking, and Di scovery", arXiv:1807:02569v1 [cs.CV], Cornell University Library, 201 Olin Library, Cornell University, Ithaca, NY 14853, (Jul. 6, 2018), 21 pgs.

"European Application Serial No. EP23193015.7 European Search Report mailed Nov. 7, 2023", 9 pages.

Kagiyama, Nobuyuki, "Machine Learning Assessment of Left Ventricular Diastolic Function Based on Electrocardiographic Features", Journal of the American College of Cardiology 76 8, (Aug. 2020), 12 pages.

Krittanawong, Chayakrit, "Artificial Intelligence in Precision Cardiovascular Medicine", J Am Coll Cardiol vol. 69 No. 21, (May 2017), 8 pages.

\* cited by examiner

ELECTROCARDIOGRAM-BASED ESTIMATION OF ECHOCARDIOGRAPHY PARAMETERS

CROSS-REFERENCE TO RELATED APPLICATIONS

This application is a continuation of U.S. patent application Ser. No. 16/948,021, filed on Aug. 27, 2020, which claims priority to and the benefit of U.S. Provisional Patent Application No. 62/894,598, filed on Aug. 30, 2019, and No. 63/065,837, filed on Aug. 14, 2020, both entitled "Left Ventricular Relaxation Risk Stratification." All applications are hereby incorporated herein by reference in their entirety.

TECHNICAL FIELD

The present disclosure relates to heart testing, and more particularly to systems, devices, and methods for determining quantitative and/or qualitative indicators of diastolic function.

BACKGROUND

Heart testing for coronary heart disease, myocardial ischemia, and other abnormal heart conditions is routinely performed using an electrocardiogram (ECG), which represents electrical potentials reflecting the electrical activity of the heart measured via electrodes placed on the patient's skin. The heart's electrical system controls timing of the heartbeat by sending an electrical signal through the cells of the heart. The heart includes conducting cells for carrying the heart's electrical signal, and muscle cells that contract the chambers of the heart as triggered by the heart's electrical signal. The electrical signal starts in a group of cells at the top of the heart called the sinoatrial (SA) node. The signal then travels down through the heart, conducting cell to conducting cell, triggering first the two atria and then the two ventricles. Simplified, each heartbeat occurs by the SA node sending out an electrical impulse. The impulse travels through the upper heart chambers, called "atria," electrically depolarizing the atria and causing them to contract. The atrioventricular (AV) node of the heart, located on the interatrial septum close to the tricuspid valve, sends an impulse into the lower chambers of the heart, called "ventricles," via the His-Purkinje system, causing depolarization and contraction of the ventricles. Following the subsequent repolarization of the ventricles, the SA node sends another signal to the atria to contract, restarting the cycle. This pattern and variations therein indicative of disease are detectable in an ECG, and allow medically trained personnel to draw inferences about the heart's condition. However, not every developing abnormality is immediately visible in an ECG, and, consequently, many patients are misdiagnosed as healthy.

A complementary test sometimes performed to evaluate heart condition is a transthoracic echocardiogram, which uses ultrasound to obtain images of the heart's valves and chambers and enables ascertaining metrics of heart movements to quantitatively assess pumping action. These metrics include, for instance, the mitral annular velocities and the transmitral flow velocities during early and late diastole. As the ventricle relaxes, the mitral annulus (a ring-like structure that separates the left atrium from the left ventricle) moves towards the base of the heart, signifying the volume expansion of the ventricle. The peak early diastolic mitral annular velocity, e', measured during early filling, is a metric of left ventricular diastolic function, and has been shown to be relatively independent of left ventricular filling pressure. In case of impaired relaxation (diastolic dysfunction), e' decreases. The peak late diastolic mitral annular velocity, a', which is measured after the early relaxation when the ventricular myocardium is passive, is a metric of atrial contraction, and may likewise serve to quantify diastolic function. In addition to the absolute values of e' and a', the early/late ratio between e' and a' can be another useful quantitative indicator. Further, during the two filling phases, there is early (E) and late (A) blood flow from the atrium to the ventricle, corresponding to the annular velocity phases. The flow is driven by the pressure difference between atrium and ventricle, and this pressure difference is a function of both the pressure drop during early relaxation and the initial atrial pressure. With minor diastolic dysfunction, the peak early diastolic transmitral flow velocity, E, is reduced in proportion to e', but if relaxation is reduced to an extent that it causes an increase in atrial pressure, E will increase again, while e', being less load-dependent, remains low. Thus, the ratio E/e' is related to the atrial pressure, and can indicate increased filling pressure (although with several reservations). In the right ventricle, this is not an important principle, as the right atrial pressure is the same as central venous pressure, which can easily be assessed from venous congestion.

Echocardiograms are currently the gold standard to diagnose diastolic dysfunction, but, at typical costs on the order of $200, they are expensive compared, e.g., with ECGs (which cost on the order of $50), and are therefore generally only used once a problem with heart function, such as a strong heart murmur or a symptom like chest pain or an irregular heartbeat, has been observed.

SUMMARY

Described herein is an approach to estimating indicators of diastolic function or dysfunction (herein also "diastolic indicators") based on ECG measurements, which enhances the utility of ECGs and obviates, in many circumstances, the need for an additional costly echocardiogram. In various embodiments, one or more machine-learned computational models trained in a supervised manner on ECG measurements correlated with parameters obtained by echocardiography (hereinafter "echocardiogram parameters") (such as, e.g., e', a', E, A, and ratios) that serve as the ground truth, operate on ECG-derived features, optionally in conjunction with patient demographic parameters (e.g., age, sex, etc.), to compute quantitative estimates of the echocardiogram parameters and/or other indicators of diastolic function. In some embodiments, the echocardiogram parameter estimates are provided as input to another layer of machine-learned computational models, or are otherwise processed, to compute one or more quantitative indices or scores (e.g., a left ventricular relaxation risk score, a lateral left ventricular relaxation index, a septal left ventricular relaxation index, or a composite left ventricular relaxation index) and/or to classify individuals' diastolic function categorically (e.g., distinguishing between normal, abnormal, or borderline function). The computational model(s) and outputs can be validated against a reference study population to determine associated statistical indicators such as prevalence probability, relative risk, likelihood ratios, or confidence intervals for predicted ranges of clinically measurable attributes, which aid risk stratification (e.g., the separation of a population into high-risk, low-risk, and rising-risk groups) and ultimately allow medical personnel to interpret the model outputs to render diagnoses for individual patients. By basing classifications, risk scores, etc., on quantitative estimates of echocardiogram parameters, which constitute metrics of diastolic dysfunction that are familiar to physicians, the described approach provides a more transparent and more granular diagnostic tool than, e.g., a machine-learned model that directly outputs a categorical assessment of diastolic function.

In accordance with various embodiments, the ECG-derived features used as input to the computational model(s) include time-frequency features derived using discrete or continuous wavelet transforms (or other time-frequency transforms) of the ECGs. Conventional ECG parameters derived directly from the time-domain ECGs, such as, e.g., Glasgow-derived parameters, may be used as additional, time-domain input features to the model. Supervised training of the computational model(s) may utilize training data that includes the ECG-derived time-frequency and time-domain features as input features, along with the ground-truth echocardiogram parameters as output labels. Alternatively, the time-frequency transform may itself be computed by a neural network model, whose output flows into neural networks implementing the computation model(s) for computing the echocardiogram parameter estimates and/or other diastolic indicators. In this case, a multi-level neural network system including a neural network for computing time-frequency transforms at the first level and one or more neural networks for computing echocardiogram parameter estimates and optionally additional diastolic indicators at one or more subsequent levels may be trained based on training data that includes the raw ECGs (along with patient demographic parameters) as input features, labeled by the ground-truth echocardiogram parameters. Beneficially, the use of time-frequency ECG features (optionally in combination with time-domain ECG features and/or patient demographic parameters), whether provided explicitly as input to a computational model or computed within a level of a multi-level computational model, can increase the accuracy of the obtained echocardiogram parameter estimates, as compared with models whose ECG-derived input is limited to time-domain features.

BRIEF DESRIPTION OF THE DRAWINGS

DESCRIPTION

The approach described herein combines conventional ECG hardware producing one or more leads, e.g., 10 electrodes and associated circuitry for a standard 12-lead ECG, with new processing functionality to derive indicators of diastolic (dys-)function. In various embodiments, the processing functionality implements one or more computational models that operate on ECGs or ECG-derived features, such as Glasgow-derived parameters and/or parameters derived using wavelet or other time-frequency transforms (e.g., short-time Fourier transform) of the ECGs, along with patient demographic parameters, and output indicators of diastolic (dys-)function, including quantitative estimates of one or more echocardiogram parameters. Beneficially, estimating the echocardiogram parameters based on features derived from ECGs (including by time-frequency transform), optionally in conjunction with patient demographic parameters, provides a cost-efficient alternative to measuring the echocardiogram parameters via electrocardiography, as is done conventionally.

Figure 1:
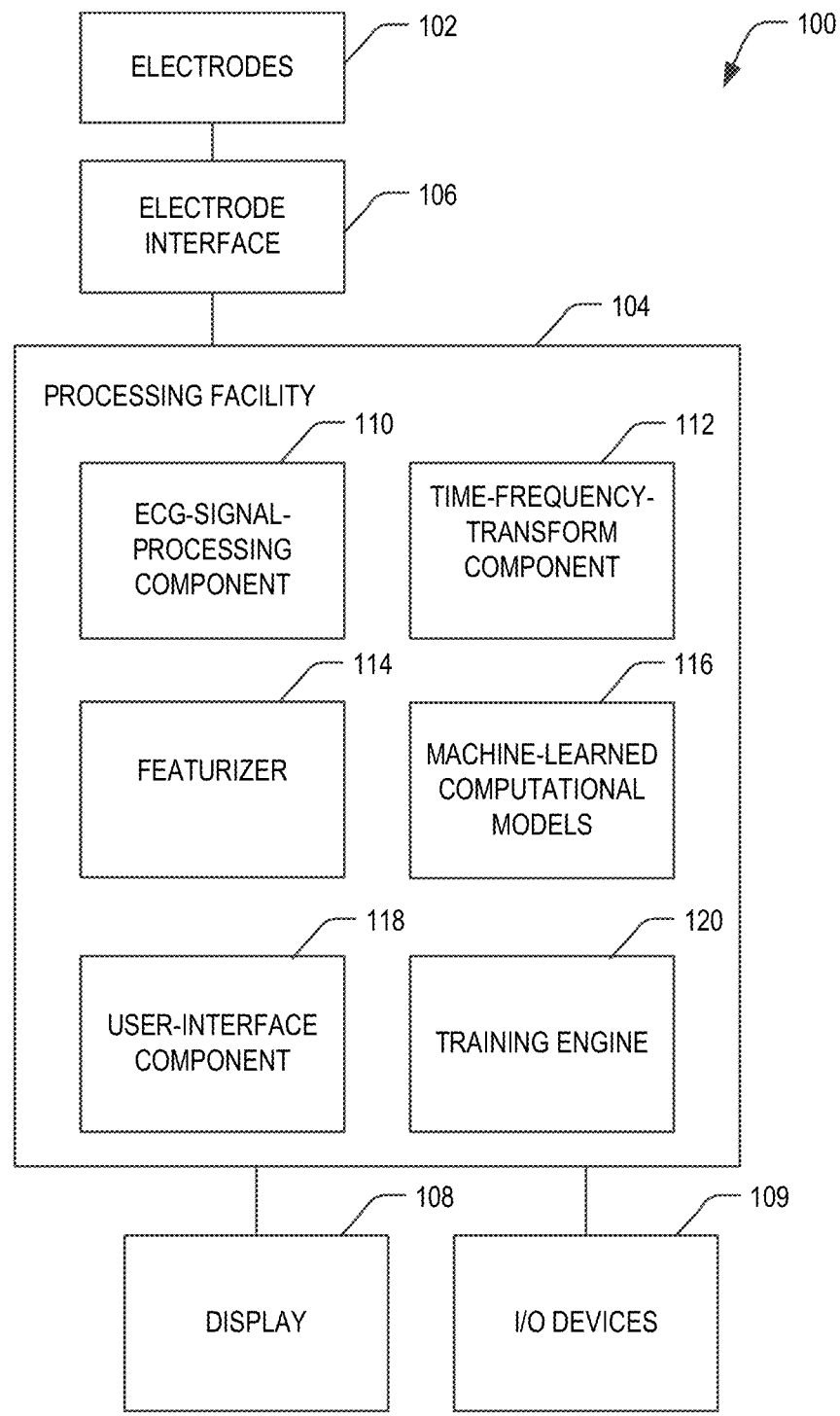
FIG. 1 is a block diagram of an example system for quantifying diastolic function, in accordance with various embodiments.

FIG. 1 is a block diagram of an example system 100 for quantifying diastolic function, in accordance with various embodiments. The system 100 includes one or more electrodes 102 for acquiring ECG signals (e.g., 10 electrodes for a traditional 12-lead ECG), a processing facility 104 for processing the ECG signals, and an electrode interface 106 connecting the electrodes 102 to the processing facility 104. The electrode interface 106 includes circuitry that outputs electrical signals suitable as input to the processing facility 104, e.g., by digitally sampling analog input signals. The system 100 further includes a display device 108 for outputting the ECG test results (including, e.g., the ECGs themselves, time-frequency maps computed therefrom, and/or various quantitative and/or qualitative indicators of diastolic function computed as described herein), and optionally other input/output devices 109, such as a keyboard and mouse and/or a printer, for instance. The display device 108 may be a touchscreen doubling as a user-input device.

The processing facility 104, electrode interface 106, display 108, and input/output devices 109 may be implemented as a single, stand-alone device implementing all computational functionality for ECG signal processing and presentation. Alternatively, they may be provided by a combination of multiple devices. For example, an ECG test device with limited functionality for recording and/or processing ECG signals received from one or more electrodes 102 via an electrode interface 106 of the device may outsource certain computationally intense processing tasks to one or more other computers. Data exchange between the ECG test device and the other computer(s) may take place via a wired or wireless network. For example, the ECG test device may be connected via the internet to a cloud-based signal-processing service. that receives the ECGs in near real time as they are being measured, or at a later time. Alternatively, the measured ECGs may be stored on a removable computer-readable medium that is subsequently read by another computer for processing. Thus, the functionality of the processing facility 104 may be distributed between multiple computational devices. Whether provided in a single device or distributed, the processing facility 104 may be implemented with a suitable combination of hardware and/or software, such as a suitably programmed general-purpose computer (including at least one central processing unit (CPU) or graphic processing unit (GPU) and associated memory); dedicated, special-purpose circuitry (such as, e.g., a digital signal processor (DSP), field-programmable gate array (FPGA), analog circuitry, or other); or a combination of both. Herein, the term "hardware processor" is used in reference to both special-purpose circuitry and general-purpose processors as used in general-purpose computers and configured via software.

The processing facility 104 may include various functionally distinct components, such as separate computer programs or functions called within a larger program flow, and/or special-purpose circuitry for certain computational tasks. These components may include an ECG-signal processing component 110 that generates ECGs for multiple leads from the (e.g., digitally sampled) ECG signals for display and analysis (e.g., by filtering, smoothing, scaling, etc., as well as by combining signals for various leads); a time-frequency transform component 112 that converts the ECG for each lead into a two-dimensional time-frequency map (signed or unsigned) and, optionally, normalizes the time-frequency map; a featurizer 114 that computes and extracts relevant parameters from the ECGs and/or the time-frequency maps for use as input features to one or more machine-learned models 116; the one or more machine-learned computational models 116, which determine echocardiogram parameter estimates and/or other diastolic indicators from these ECG-derived features in conjunction with patient demographic parameters; and/or a user-interface 118 component that generates graphic representations of the data provided by the other modules and assembles them into a screen for display (as shown, e.g., in FIGS. 9 and 10). The ECG-signal-processing component 110 may be a conventional processing module as used in commercially available heart monitors and/or as is capable of straightforward implementation by one of ordinary skill in the art. The time-frequency transform component 112, featurizer 114, and computational models 116 implement algorithms and provide functionality explained further below, and can be readily implemented by one of ordinary skill in the art given the benefit of the present disclosure.

For purposes of the creating the machine-learned models 116, some instances of the processing facility 104 also include a training engine 120 that implements one or more suitable machine-learning algorithms to build and/or train (that is, determine adjustable parameters of) the models 116 based on training data. Suitable training algorithms for various types of models are well-known to those of ordinary skill in the art. For example, a neural network model may be trained using backpropagation of errors, e.g., with stochastic gradient descent. Note that, once the machine-learned models 116 have been trained and their parameters are fixed, the training engine 120 is no longer used; accordingly, the training engine 120 may be omitted from a processing facility 104 configured for assessing diastolic function of patients in the inference phase.

As will be readily appreciated, the depicted components reflect merely one among several different possibilities for organizing the overall computational functionality of the processing facility 104. The components may, of course, be further partitioned, combined, or altered to distribute the functionality differently. The various components may be implemented as hardware components, software components (e.g., executed by a general-purpose processor), or a combination of both. For example, it is conceivable to implement the time-frequency transform component 112 (which generally involves the same operations for each incoming ECG signal) and/or certain machine-learned computational models 116 with special-purpose circuitry to optimize performance, while implementing other components in software.

Figure 2:
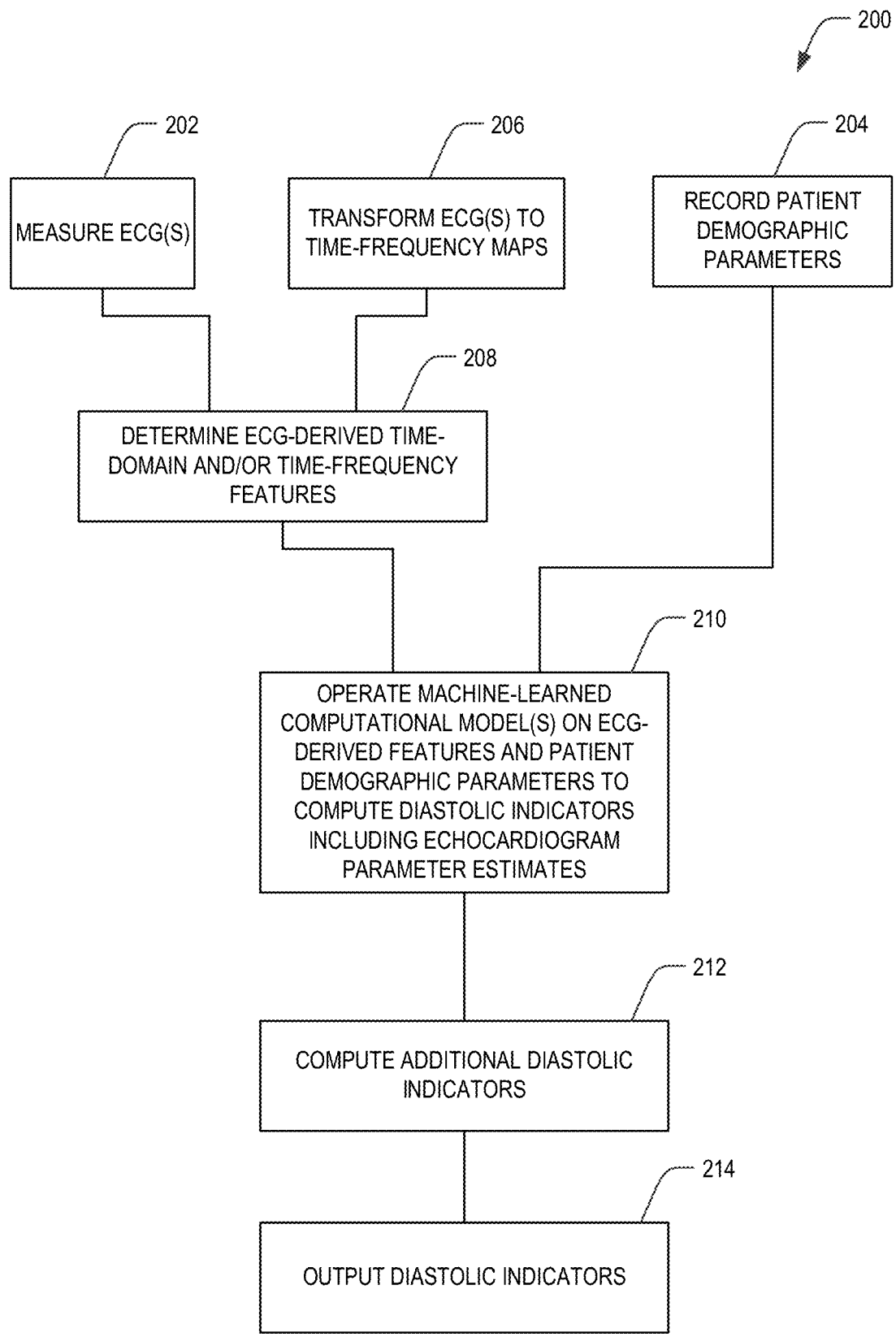
FIG. 2 is a flow chart of an example method for quantifying diastolic function using echocardiogram parameter estimates computed from electrocardiograms, in accordance with various embodiments.

FIG. 2 is a flow chart of an example method 200 for quantifying diastolic function using echocardiogram parameter estimates computed from electrocardiograms, in accordance with various embodiments. The method 200 begins, in acts 102 and 104, with measuring one or more ECGs for a patient (act 102) and recording relevant patient demographic parameters (such as, e.g., age, sex, height, weight, health conditions such as hypertension, or other factors that might affect how the patient's diastolic functions is reflected in ECGs and parameters derived from ECG) (act 204). The term "ECG" in the singular is herein generally used in reference to an individual lead; and multiple ECGs measured for a patient may, accordingly, correspond to multiple respective leads. For example, from ECG signals measured with ten electrodes in a standard configuration, ECGs for twelve leads can be computed in a manner routinely used in the medical arts. It is to be understood, however, that the method described herein does not require the use of all twelve leads, but is generally applicable to any number of ECGs, such as any subset of the standard twelve leads.

In accordance with the standard configuration, four of the ten electrodes (conventionally labeled LA, RA, LL, RL) are placed on the patient's left and right arms and legs; two electrodes (labeled V1 and V2) are placed between the fourth and fifth ribs on the left and right side of the sternum; a further, single electrode (labeled V3) is placed between V2 and V4 on the fourth intercostal space; one electrode (labeled V4) is placed between the fifth and sixth ribs at the mid-clavicular line (the imaginary reference line that extends down from the middle of the clavicle), and, in line therewith, another electrode (labeled V5) is positioned in the anterior axillary line (the imaginary reference line running southward from the point where the collarbone and arm meet), and the tenth electrode (labeled V6) is placed on the same horizontal line as these two, but oriented along the mid-axillary line (the imaginary reference point straight down from the patient's armpit). The electric potentials measured by electrodes V1 through V6 correspond to six of the twelve standard leads; the remaining six leads correspond to the following combinations of the signals measured with the individual electrodes: I=LA−RA; II=LL−RA; III=LL−LA; aVR=RA−½(LA+LL); aVL=LA−½(RA+LL); and aVF=LL−½(RA+LA).

With reference again to FIG. 2, the method 200 further involves transforming the ECGs (immediately upon measurement, or at a later time after storage in memory) into two-dimensional time-frequency maps by a suitable mathematical transform, such as, for instance, wavelet transform or short time Fourier transform, in act 206. In certain embodiments, a continuous wavelet transform (CWT) is used. For a given continuous ECG x(t), the CWT is given by:

$$W(a, b) = \frac{1}{\sqrt{a}} \int_{-\infty}^{+\infty} \overline{\psi\left(\frac{t-b}{a}\right)} x(t) dt,$$

where ψ is a selected wavelet, b corresponds to a shifted position in time and a to a scaling factor, and W(a, b) is the two-dimensional function of position in time and scale resulting from the transform, also called wavelet coefficients. Similarly, for a discretized ECG x(k) (where k is an integer), the CWT is given by:

$$W(a, b) = \frac{1}{\sqrt{a}} \sum_k x(k) \left( \int_{-\infty}^{(k+1)T} \overline{\psi\left(\frac{t-b}{a}\right)} dt - \int_{-\infty}^{kT} \overline{\psi\left(\frac{t-b}{a}\right)} dt \right),$$

where T is the sampling period. The wavelet selected for processing may be, for example, a Mexican hat wavelet, Morlet wavelet, Meyer wavelet, Shannon wavelet, Spline wavelet, or other wavelet known to those of ordinary skill in the art. The CWT W(a, b) is also referred to as a scalogram. The time-frequency maps (such as, e.g., scalograms) generally include both positive and negative values, i.e., they are "signed." In some embodiments, the absolute value of the signal value (or the square of the signal value) is taken at each time-frequency point, resulting in an "unsigned" time-frequency map.

The ECGs and time-frequency maps are processed, in act 208, to extract parameters to be provided, along with the patient demographic parameters, as input features to one or more machine-learned computational models. Time-domain features extracted directly from the ECGs may include, for example (and without limitation), the extrema, durations, or area of any of the P, Q, R, S, or T waves, or signal amplitudes at one or more specified points in time associated with the P, Q, R, S, or T waves. The input to the models may also include conventional ECG-derived parameters, such as Glasgow parameters. Time-frequency features extracted from the time-frequency maps may include any or all of the time-frequency coefficients (e.g., wavelet coefficients) themselves or any parameters derived from the time-frequency maps, for example (and without limitation), extrema across frequency at one or more points in time associated with the P, Q, R, S, or T waves, extrema across time at one or more specified points in frequency, or integral measures associated with extrema in the time-frequency map. U.S. Pat. No. 9,700,226, filed on Sep. 20, 2016, which is incorporated herein by reference, describes time-frequency transforms of ECGs (in particular CWTs) and various parameters derived from the resulting time-frequency maps that may be used as input features. In general, time-frequency features may be extracted from the signed or unsigned time-frequency map or a combination of both. Further, both the time-domain and the time-frequency features may include parameters derived from individual heartbeats across synchronized ECGs for different leads and from beat to beat. For example, a single parameter derived from the T wave may be obtained for each lead and for multiple heartbeats. In this example, using twelve leads and twenty recorded heartbeats, such a single parameter would yield 12·20=240 features. An additional single parameter obtained for the R wave would become another 240 features, etc. A set of features corresponding to the same parameter measured across multiple leads captures the phase differences between leads, which can provide important comparisons useful as input to the computational models. Values of a single parameter measured over multiple heartbeats may be combined into a single aggregated feature, e.g., the average or median across the multiple heartbeats.

Figure 4:
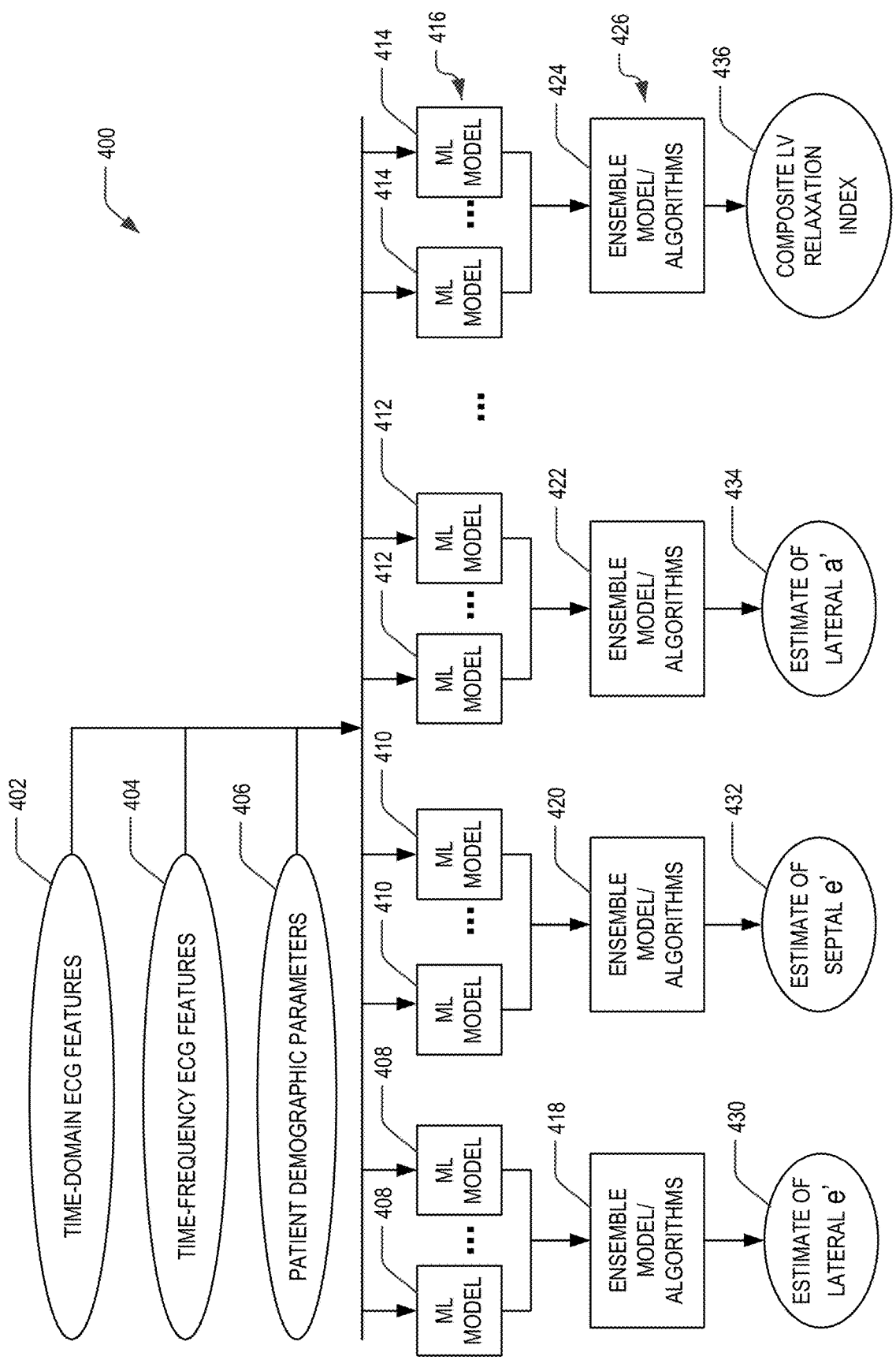
FIG. 4 is a data flow diagram illustrating an example two-level computational model architecture for computing echocardiogram parameter estimates, in accordance with various embodiments.

In act 210, one or more machine-learned computational models (e.g., implemented by component 116 of system 100) operate on the ECG-derived features (including the time-frequency features) and patient demographic parameters to compute one or more diastolic indicators, including one or more estimates of echocardiogram parameters (e.g., e', a', E, A, and ratios). Multiple computational models (potentially of different types) may be used to compute different respective parameter estimates and indicators. In various embodiments, multiple computational models are organized in a one-level structure or, alternatively, in a hierarchy of two or more levels. FIG. 4 (described below) provides an example of a two-level hierarchy. Further, individual indicators may be computed with a multi-level hierarchy of models, the number of models and/or levels generally being different for each indicator. In a two-level hierarchy for an individual indicator, different models may, for instance, be used to compute a first set of estimates, and an ensemble model may then be used at the second level to combine the first set of estimates into a final estimate. The estimates of the echocardiogram parameters are continuous-variable estimates that may be computed with regression models or may, alternatively, be piecewise approximated using classification models. In general, the computational model(s) may include, e.g., decision trees or random forests, neural networks, regression analysis, Bayesian networks, or other suitable machine-learning models known to those of ordinary skill in the art. Regression models that were found, in some embodiments, to provide particularly good performance in estimating the echocardiogram parameters include random forest and least squares models.

The echocardiogram parameter estimate(s) output by the computational model(s) may flow as inputs into further algorithms and/or additional machine-learned computational models for computing, in act 212, additional diastolic indicators, such as qualitative classifications of diastolic function (e.g., a three-level classification between normal, borderline, and abnormal diastolic function; or a 5-level classification between low-possibility, possible, borderline, probable, and highly probable LV relaxation abnormality), and/or quantitative indicators such as left ventricular (LV) relaxation risk score(s), LV relaxation indices (e.g. lateral, septal, and/or average/composite indices, etc.). If machine-learned computational models are used for this purpose, these models form, along with the computational models for computing the echocardiogram parameter estimates in act 210, a two-level hierarchical architecture (optionally with sub-levels at one or both levels), e.g., as illustrated by way of example in FIG. 5 (described below). Further, in some embodiments, certain qualitative and/or quantitative diastolic indicators (such as classifications or LV relaxation indices) are computed along with the echocardiogram parameter estimates by the (first level of) computational models in act 210, and flow, along with the echocardiogram parameter estimates, into downstream computations.

The computation of additional diastolic indicators in act 212 need not necessarily utilize machine-learned models. For example, echocardiogram parameter estimates may be scaled to indices spanning a fixed range (e.g., from 0 to 100). As another example, echocardiogram parameter estimates may be compared against specified thresholds to classify diastolic function between various degrees or likelihoods of abnormality. For example, one measure of left ventricular diastolic dysfunction is low e'. (See "Recommendations for the Evaluation of Left Ventricular Diastolic Function by Echocardiography: An Update from the American Society of Echocardiography and the European Association of Cardiovascular Imaging," J Am Soc Echocardiogr 2016; 29:277-314.) Low e' is defined as septal e' velocity<7 cm/s or lateral e' velocity<10 cm/s, where septal e' is the velocity of the septal mitral annular motion at early diastole and lateral e' is the velocity of the lateral mitral annular motion. Ordinarily, septal and lateral e' are measured via transthoracic echocardiography, but they can be estimated, in accordance herewith, from ECGs. The estimated septal and lateral e' parameters may be compared against values of 7 or 10 (in cm/s), respectively, to classify diastolic function as normal or abnormal. Optionally, the threshold values for comparison against the estimated e' parameters may be set lower or higher than those used with the parameters obtained by echocardiography to account for any error in the estimate and provide higher confidence for normal and abnormal classifications, with a region of uncertainty in between.

Figure 9:
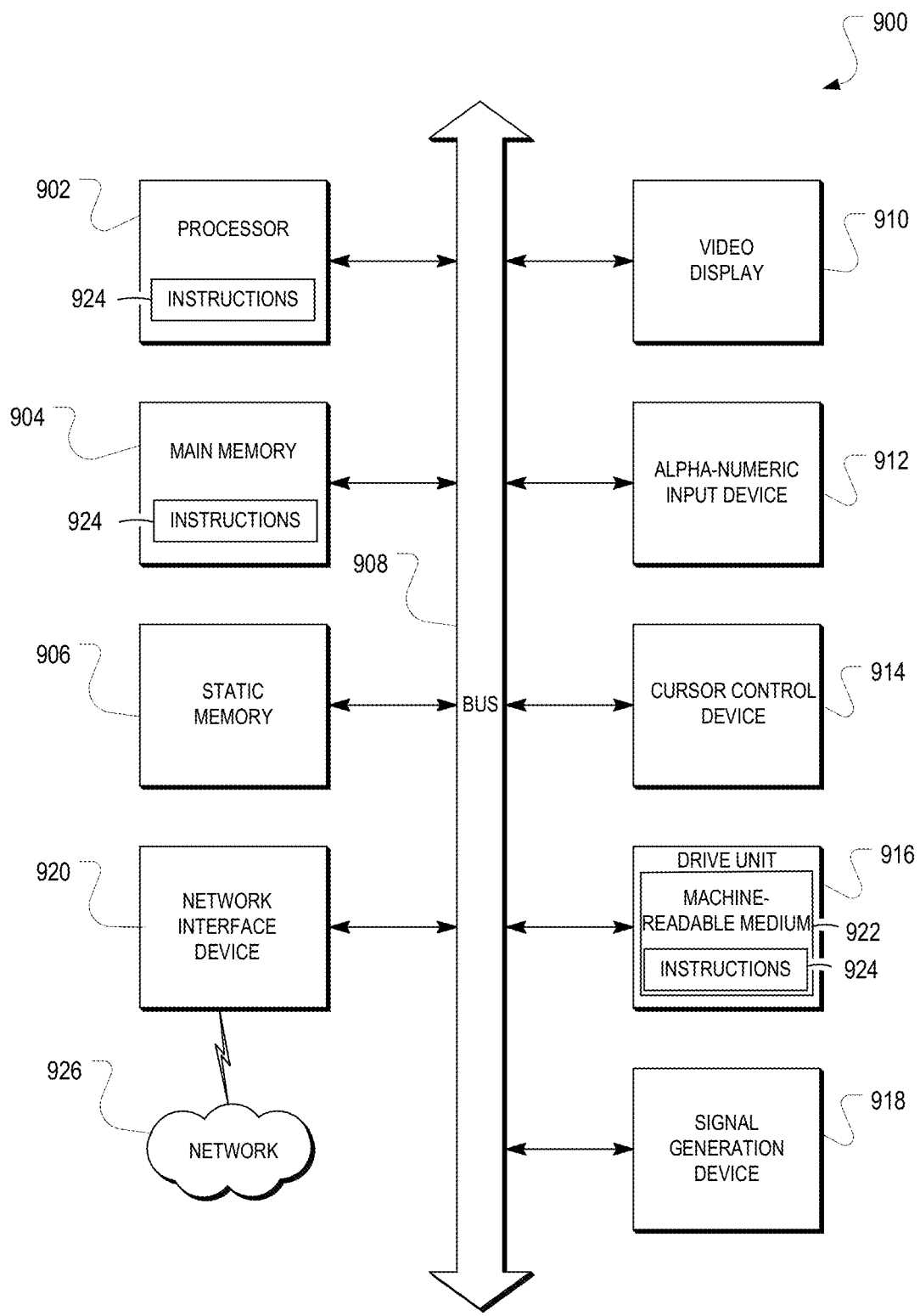
FIG. 9 is a block diagram of an example computer system as may serve as processing facility in accordance with various embodiments.

The echocardiogram parameter estimates and/or other diastolic indicators computed in acts 210, 212 may be provided as output (e.g., displayed on screen, printed, sent via electronic notification, etc.) to a physician or other clinical personnel in act 214, optionally along with the ECGs and/or time-frequency maps from which these indicators have been computed. FIGS. 9 and 10 provide example output displays.

To aid interpretation of the diastolic indicators, statistical metrics determined by validating the diastolic indicators against a reference study population may be provided. Such metrics may include, e.g., statistical indicators such as prevalence probability, relative risk, likelihood ratios, or confidence intervals for predicted ranges of clinically measurable attributes.

Prevalence probability is a measure of the probability that a person with a certain test result has a certain condition, determined using a reference study population, and can be calculated by dividing the number of persons with the same test results that have the condition in the reference study population by the total number of persons with the same test result in the reference study population.

Relative risk is a ratio of the probability of an event occurring in a particular sub-group (Group A) of a population versus the probability of the event occurring in a reference sub-group (Group B) of the same population that is independent of the sub-group being studied (i.e., Group A and Group B are independent sub-groups within the same population), and can be calculated, accordingly, by dividing the probability of the event in Group A by the probability of the event in Group B.

Likelihood ratios (LR) in medical testing are used to interpret diagnostic tests by indicating how likely a patient has a disease or condition. The higher the ratio, the more likely the patient has the disease or condition. Conversely, a low ratio means that the patient very likely does not have the disease or condition. Therefore, these ratios can help a physician rule in or rule out a disease. A likelihood ratio is calculated by dividing the probability that a person with the condition has a certain test result by the probability that a person without the condition has that test result.

Confidence intervals demonstrate a range of values that a predicted measure (such as, e.g., a diastolic indicator) may actually fall between with a certain degree of confidence. Typically, if a dataset follows a normal distribution, then these intervals are calculated using statistical techniques based on formulas that are widely accepted for normally distributed datasets. The most common confidence intervals used in medicine are 95% and 70% confidence intervals since they are easily calculated using a mean and standard deviation derived from the overall dataset. Confidence intervals are used in risk-stratification by examining how much of the overall interval lies in the clinically accepted normal or abnormal range. Confidence intervals can also be used for rule-in or rule-out assessments if the 95% confidence interval lies completely to one side or the other of a clinically accepted threshold. A 70% confidence interval corresponds to the population mean+/−the population standard deviation. A 95% confidence interval corresponds to the population mean+/−twice the population standard deviation.

Figure 3:
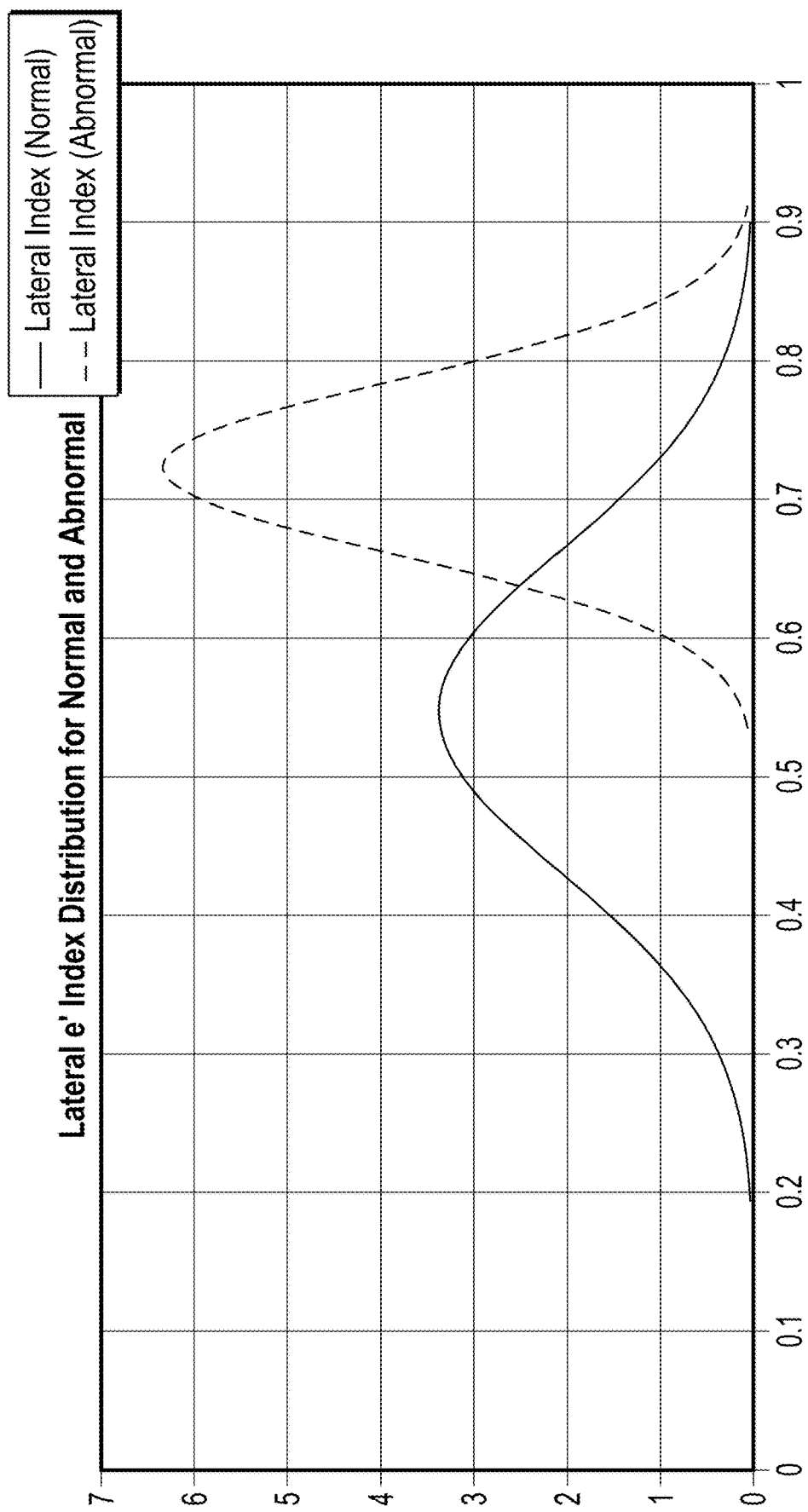
FIG. 3 shows plots of example lateral left ventricular relaxation index distributions for normal and abnormal patient populations, illustrating an example diastolic indicator useful for risk stratification in accordance with one embodiment.

FIG. 3 shows example distribution plots 300, 302 of the lateral LV relaxation index (along the independent axis) for "normal" and "abnormal" patient populations, respectively, based on calculated averages and standard deviations. The plots demonstrate that the lateral LV relaxation index, indeed, has risk-stratification value, especially for normal patients. The abnormal plot 302 overlaps significantly with the normal plot 300 (by about 30% of the normal plot), but the plots 300, 302 can nonetheless be used to calculate both percentile differences and likelihood ratios. While FIG. 3 shows distribution plots for, specifically, the lateral LV relaxation index, other LV relaxation indices exhibit similar behavior.

FIG. 4 is a data flow diagram illustrating an example two-level computational model architecture 400 for computing echocardiogram parameter estimates, in accordance with various embodiments. In this figure, as well as in FIGS. 5 and 6 explained below, rectangles generally indicate computational blocks, while ovals generally indicate data provided as input to or resulting as output from these blocks. The two-level architecture 400 takes a combination of conventional and/or other time-domain ECG features 402, time-frequency features 404 selected or derived from time-frequency transform(s) of the ECG(s), and patient demographic parameters 406 as input into multiple machine-learned computational models 408, 410, 412, 414 ("ML models") at the first level 416 of the hierarchy 400. Different models may operate on different subsets of the input features 402, 404, 406. Outputs of the first-level models 408, 410, 412, 414 flow as inputs into respective ensemble models 418, 420, 422, 424 at the second level 426 of the hierarchy. The ensemble models 418, 420, 422, 424 each compute one of various diastolic indicators from the first-level outputs (optionally augmented by some or all of the first-level feature inputs 402, 404, 406). For example, as shown, a number of computational models 408 (which generally include models of different types, e.g., random-forest, least-squares, and neural network models) may provide first-level estimates of lateral e', which are then further processed, in the associated ensemble model/algorithm 418, to compute a final estimate 430 of lateral e'. Combining the results of multiple computational models in this manner may achieve higher-accuracy estimates than one model alone. Similarly, other echocardiogram parameter estimates 432, 434, e.g., as shown, for septal e' and a', can be computed by two levels of computational and ensemble models (e.g., models 410, 422 to compute septal e' 432 and models 412, 422 to compute a' 434). Further, as shown, the two-level architecture 400 may include models 414, 424 to compute other diastolic indicators, e.g., as shown, a composite LV relaxation index 436, directly from the inputs 402, 404, 406.

In general, the first-level computational models 408, 410, 412, 414 may include binary (2-class), multi-class (e.g., 3-class or 5-class), or regression (continuous-variable) models, and the second-level computational models may include ensemble models 418, 420, 424, 426. Each ensemble model 418, 420, 424, 426, in turn, may include one or more binary, multi-class, and/or regression models, optionally augmented by logic, equations, formulas, or algorithms to further refine the accuracy of the first-level models.

Figure 5:
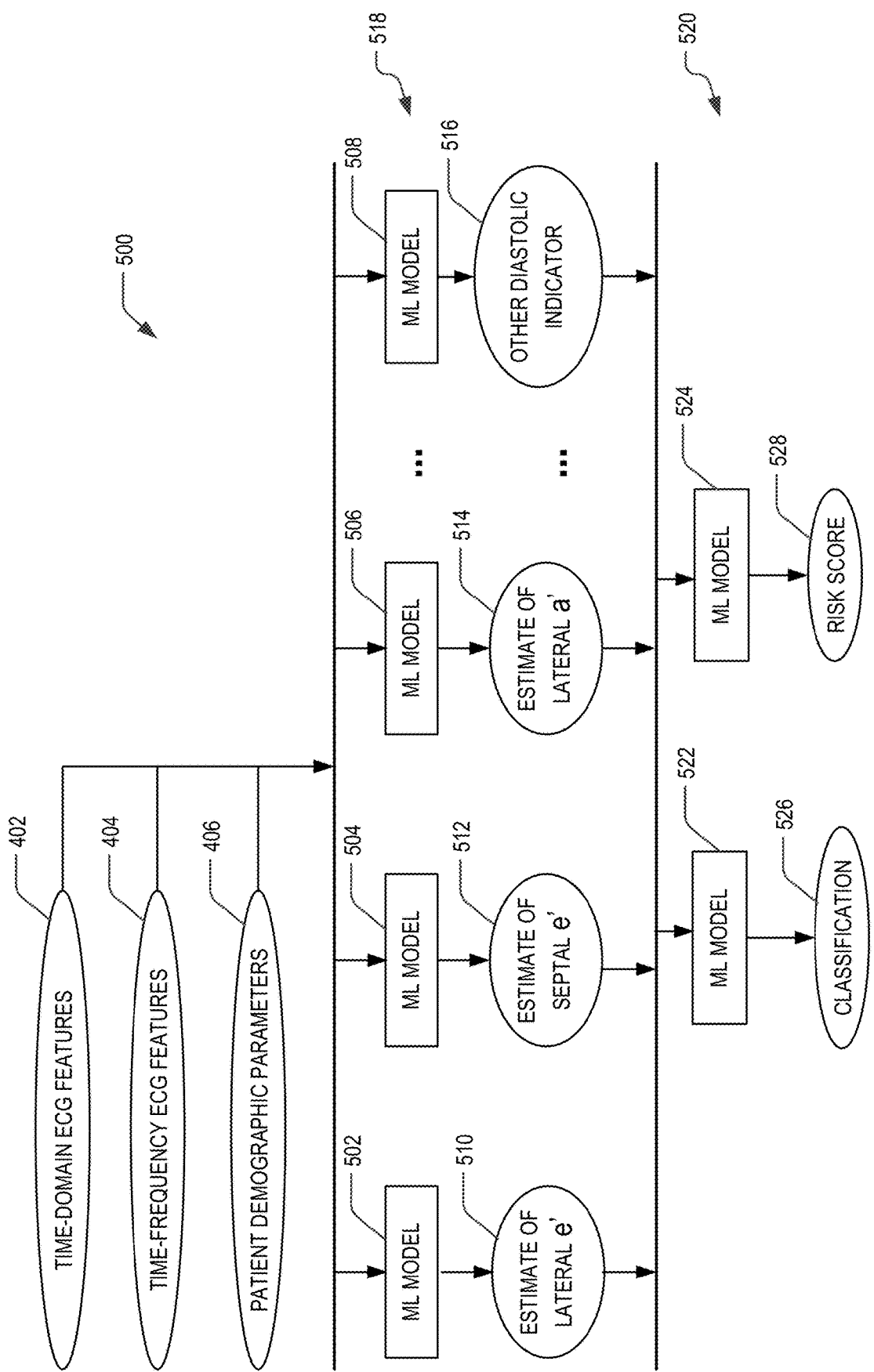
FIG. 5 is a data flow diagram illustrating an example two-level computational model architecture for computing various diastolic indicators using echocardiogram parameter estimates, in accordance with various embodiments.

FIG. 5 is a data flow diagram illustrating an example two-level computational model architecture 500 for computing various diastolic indicators using echocardiogram parameter estimates, in accordance with various embodiments. Herein, machine-learned computational models 502, 504, 506, and optionally 508 operate on the ECG-derived features 402, 404 and patient demographic parameters 406 to generate echocardiogram parameter estimates 510, 512, 514 (e.g., as shown, lateral and septal e', as well as a') and optionally other diastolic indicators 516 at the output of the first level 518. These echocardiogram parameter estimates 510, 512, 514 and/or other diastolic indicators 516 are then provided as input to a second level 520 of machine-learned computational models 522, 524, which compute various downstream categorical or quantitative diastolic indicators, e.g., as shown, a normal/borderline/abnormal classification 526 or risk score 528. Different selections and combinations of the first-level outputs may be relevant for different ones of the downstream diastolic indicators.

As will be appreciated by those of ordinary skill in the art, the levels 518, 520 for computing first-level echocardiogram parameter estimates 510, 512, 514 and downstream second-level diastolic indicators 526, 528, respectively, may each include multiple sub-levels. For example, the architectures 400, 500 can be used in combination, such that each of the computational models 502, 504, 506, 508 for computing, e.g., echocardiogram parameter estimates is implemented by two sub-levels corresponding to models of the levels 416, 426 of the architecture 400. Thus, the model 502 for computing lateral e', for instance, may include a two-level structure of models 408, 418.

The one or more models (e.g., model architectures 400, 500) may be developed using machine-learning training processes, such as supervised learning. Training data to be used in the training process may be obtained from a (generally large) number of patients whose diastolic function spans a range from normal function to a high degree of abnormal (or dys-)function. For each patient, both one or more ECGs and one or more echocardiograms are acquired. The ECGs are processed to derive conventional/time-domain as well as time-frequency parameters to be used as input features to the model(s), and the echocardiograms are processed to derive one or more echocardiogram parameters of interest that will serve as the ground truth for training. The training dataset includes pairs of a set of input features and a set of output labels for each patient, the input features including the ECG-derived parameters as well as any relevant patient demographic parameters, and the output labels including the echocardiogram parameters for that patient. To train a model (e.g., one of the models 408, 410, 412) to estimate a given echocardiogram parameter, the input features are fed into the model, and the model-generated output is compared against the ground-truth echocardiogram parameter; the discrepancy between the measured (ground-truth) and estimated echocardiogram parameters is used as feedback to iteratively adjust the model. To directly train a model for another type of diastolic indicator, such as a classification or risk score, ground-truth classifications or scores may be determined for each patient, e.g., from the measured echocardiogram parameters. Training algorithms for building and training various types of models are well-known to those of ordinary skill in the art.

Model development may also incorporate various feature-reduction techniques, such as hyper-parameter tuning, random forest feature importance, de-correlation, principal component analysis (PCA), clustering, minimum redundancy maximum relevance, mean-0 normalization, min-max normalization, etc. Feature-reduction analysis is done during the model training process for each model individually to select the most useful features for that model and discard the others which have lower predictive qualities for the target value of the model (which is the parameter that the model is intended to predict). For example, the training process may initially operate on hundreds of input features, whose relative contributions to accurately predict the target parameter are quantitatively assessed to reduce the input feature set to merely tens of features. Feature reduction performed during training of various models has shown that, in general, time-frequency features contribute significantly to the accuracy of the echocardiogram parameter estimates. In some embodiments, the feature set retained at the completion of feature-reduction analysis includes at least one third time-frequency features, and less than 20% patient-demographic features, the remainder being traditional ECG features. In one example embodiment, a set of eighteen features selected as input to a model for estimating e' includes about 39% time-frequency features.

So far, it has been assumed that the time-frequency features flowing into the computation of echocardiogram parameter estimates and/or other diastolic indicators are computed explicitly and provided to the machine-learned computational model(s) as input features. Alternatively, it is possible to utilize time-frequency information implicitly by structuring the models in a manner that extracts relevant time-frequency parameters. For example, the computational models may be implemented as a multi-level neural network system including a neural network for computing a time-frequency transform at the first level and one or more neural networks for computing echocardiogram parameter estimates and optionally additional diastolic indicators at the subsequent second level (which, as explained above, may itself include multiple (sub-)levels).

Figure 6:
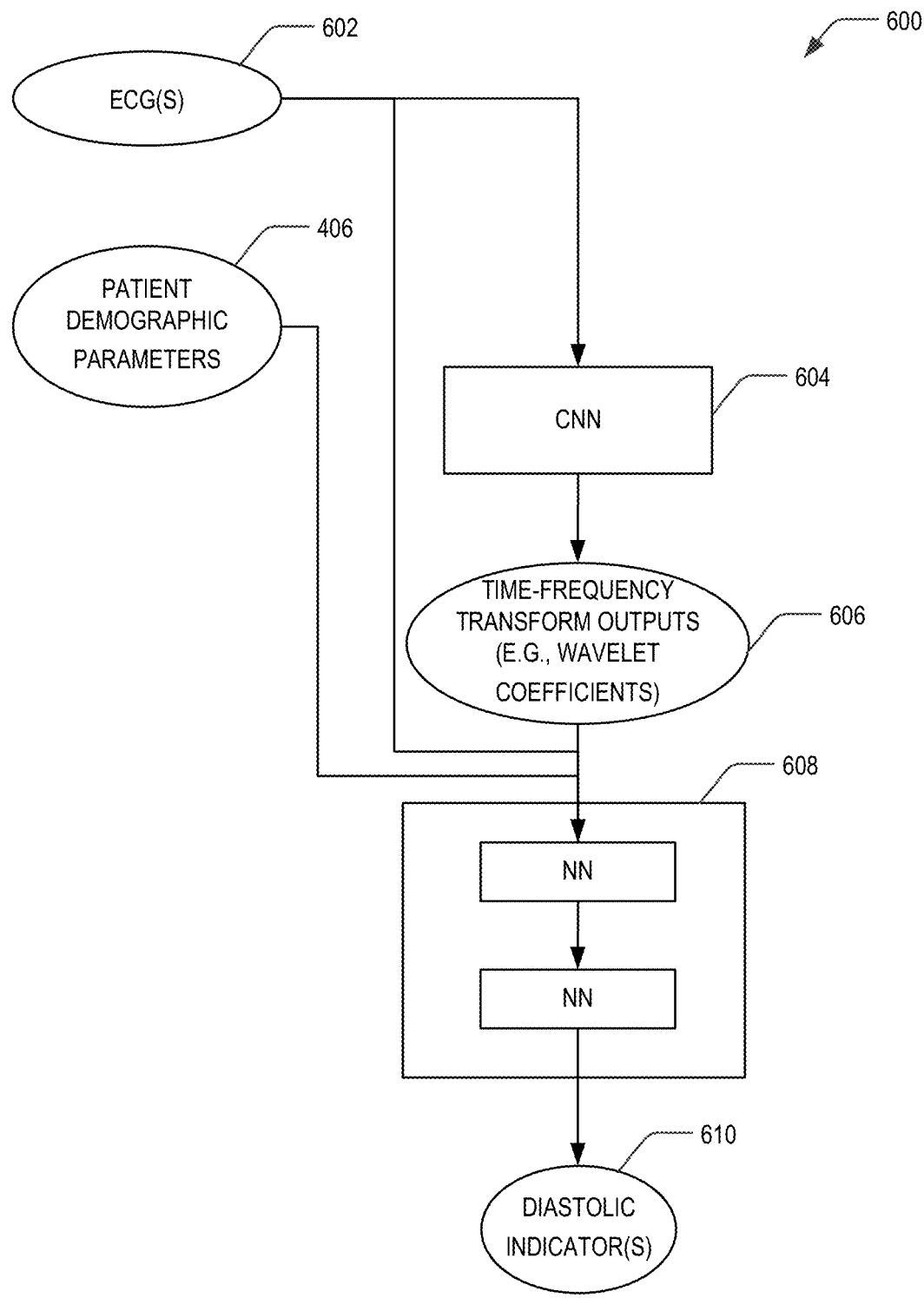
FIG. 6 is a data flow diagram illustrating an example two-level neural network architecture 600 for computing diastolic indicators from raw electrocardiograms using an implicit time-frequency transform, in accordance with various embodiments.

FIG. 6 is a data flow diagram illustrating an example two-level neural network architecture 600 for computing diastolic indicators from one or more raw ECGs 602, using an implicit time-frequency transform, in accordance with various embodiments. At the first level, a convolutional neural network (CNN) 604 may be configured to compute a time-frequency transform 606 for each ECG 602. For example, to compute the CWT of an ECG 602, the weights of the CNN 604 may be chosen to be the wavelets $\psi$ evaluated across a range of different values of the scaling factor $\alpha$. In the case of a 8192-sample ECG with 64 CWT scales a, there are 8192 inputs to the convolutional layer and 64 rows of 8192 neurons for a total of $8192 \cdot 64 = 524288$ outputs, which constitute the wavelet coefficients W(a, b), that is, the outputs 606 of the time-frequency transform (which constitute, technically, the output layer of the CNN, but are herein depicted separately for emphasis). These outputs 606 flow as inputs into one or more neural networks 608 at the second level, which compute diastolic indicators 610, including, in accordance with various embodiments, one or more echocardiogram parameter estimates. As symbolically indicated, the second-level neural network(s) 608 may include multiple sub-levels, e.g., similar to the example architectures 400, 500. (Further, although not explicitly shown, the neural network(s) 608 may include multiple parallel branches of neural networks for determining multiple echocardiogram parameter estimates or other diastolic indicators.) However, in contrast to the computational model architectures 400, 500, which take time-domain and time-frequency features as input, the neural networks 604, 608 operate on the raw ECGs 602, and feature selection is performed implicitly as part of the application of the neural network(s) 608 at the second level. More specifically, as shown, inputs to the second-level neural network(s) 608 may include the outputs 606 of the time-frequency transform implemented by the CNN 604 (all of these outputs constituting time-frequency features) as well as, optionally, the raw ECGs 602 and/or patient demographic parameters 406. By virtue of network weight adjustments made during training, the second-level neural network(s) 608 may be configured to implicitly derive time-domain features from the ECG(s) 602 and select or derive time-frequency features from the time-frequency transform outputs 606 in one or more initial network layers, with subsequent layers of the neural network(s) 608 operating on these features.

The neural network(s) 608 for computing the diastolic parameters may be implemented by various types of neural networks known to those of ordinary skill in the art, which may be selected depending, e.g., on the particular diastolic indicator. Neural networks suitable for computing echocardiogram parameter estimates and/or other diastolic indicators include, for example and without limitation, multi-layer perceptrons (MLPs) and probabilistic neural networks (PNNs) based on dynamic decay adjustment (DDA). MLPs can learn non-linear function approximators for classification or regression, and may (in contrast to logistic regression) include one or more non-linear hidden layers between the input and output layers. PNNs may be created using an algorithm, known as "constructive training of PPNs," that generates rules based on numerical data, each rule defining a high-dimensional Gaussian function that is adjusted by two thresholds to avoid conflicts with rules of different classes.

The neural networks 604, 608 of the two-level neural network architecture 600 may be trained in a supervised manner based on ECGs (and, optionally, patient demographic parameters) paired with ground-truth echocardiogram parameters (as measured by echocardiography). The weights of the CNN 604 are initialized in accordance with the desired time-frequency transform, e.g., to the selected wavelets of a CWT. The weights of the subsequent neural network(s) 608 may be initialized in multiple ways, e.g., with random weights, and are adjusted during training. Training may also include modifying the weights of the CNN 604. In principle, the combined, two-level neural network architecture 600 may be trained end-to-end from the initial weights, e.g., using back propagation (which is well-known in the art) all the way through the CNN 604. It may be beneficial, however, to instead train the networks 604, 608 in two stages: In the first stage, the weights of the CNN 604 may be held fixed to provide the time-frequency transform outputs 606 (e.g., wavelet coefficients) to be input to the second-level neural network(s) 608, which may be trained, e.g., using back propagation stopping at the output of the CNN 604. In this manner, the second-level neural network(s) 608 can benefit from the spectral information provided by the time-frequency transform(s). After training the second-level neural-networks 608, the restriction of fixing the weights of the CNN 604 at the first level can be relaxed, and the combined two-level system of neural networks 604, 608 can be trained to adjust the weights at both levels.

Figure 7:
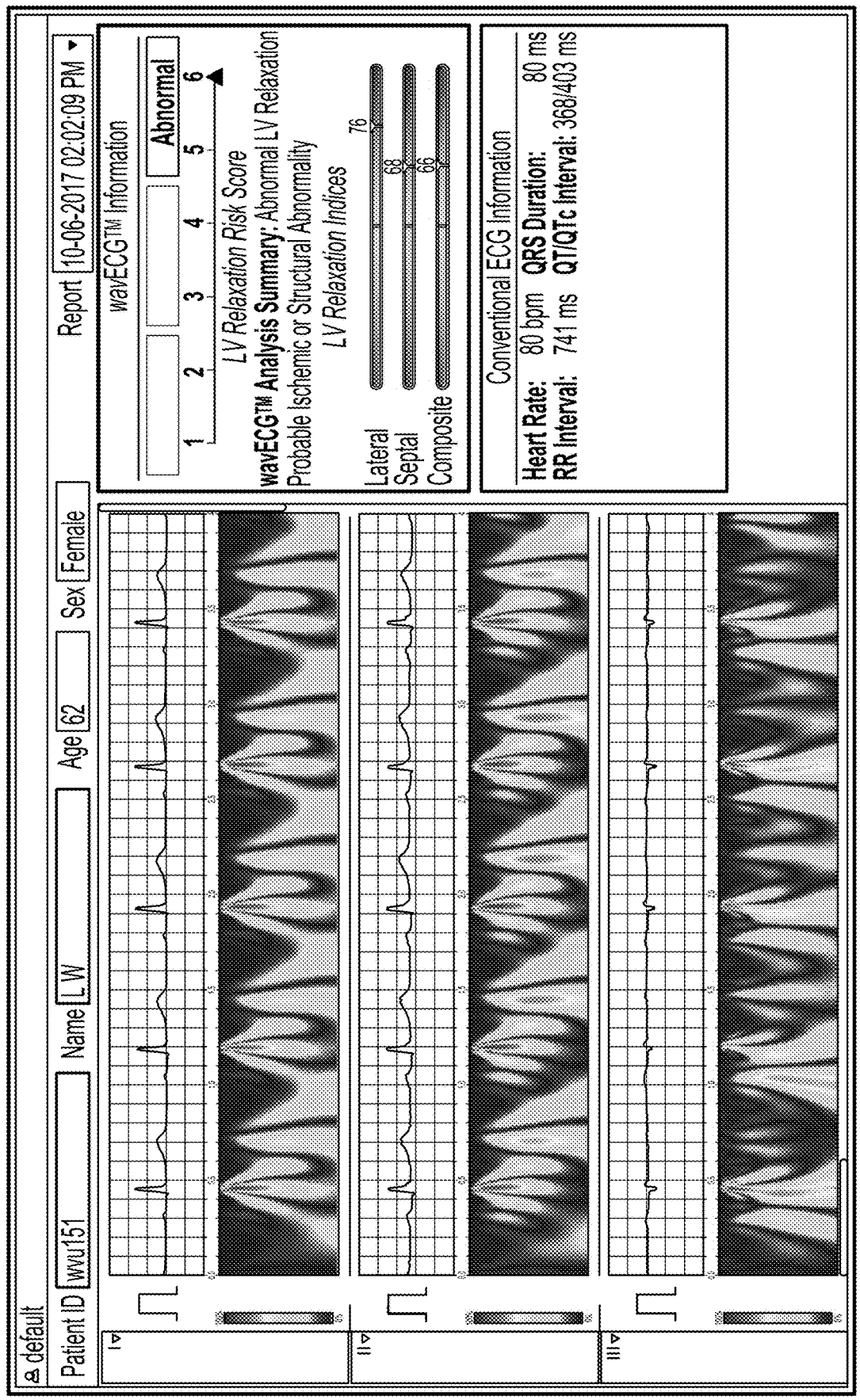
FIG. 7 is a user interface showing an example report screen for an abnormal case in accordance with various embodiments.
Figure 8:
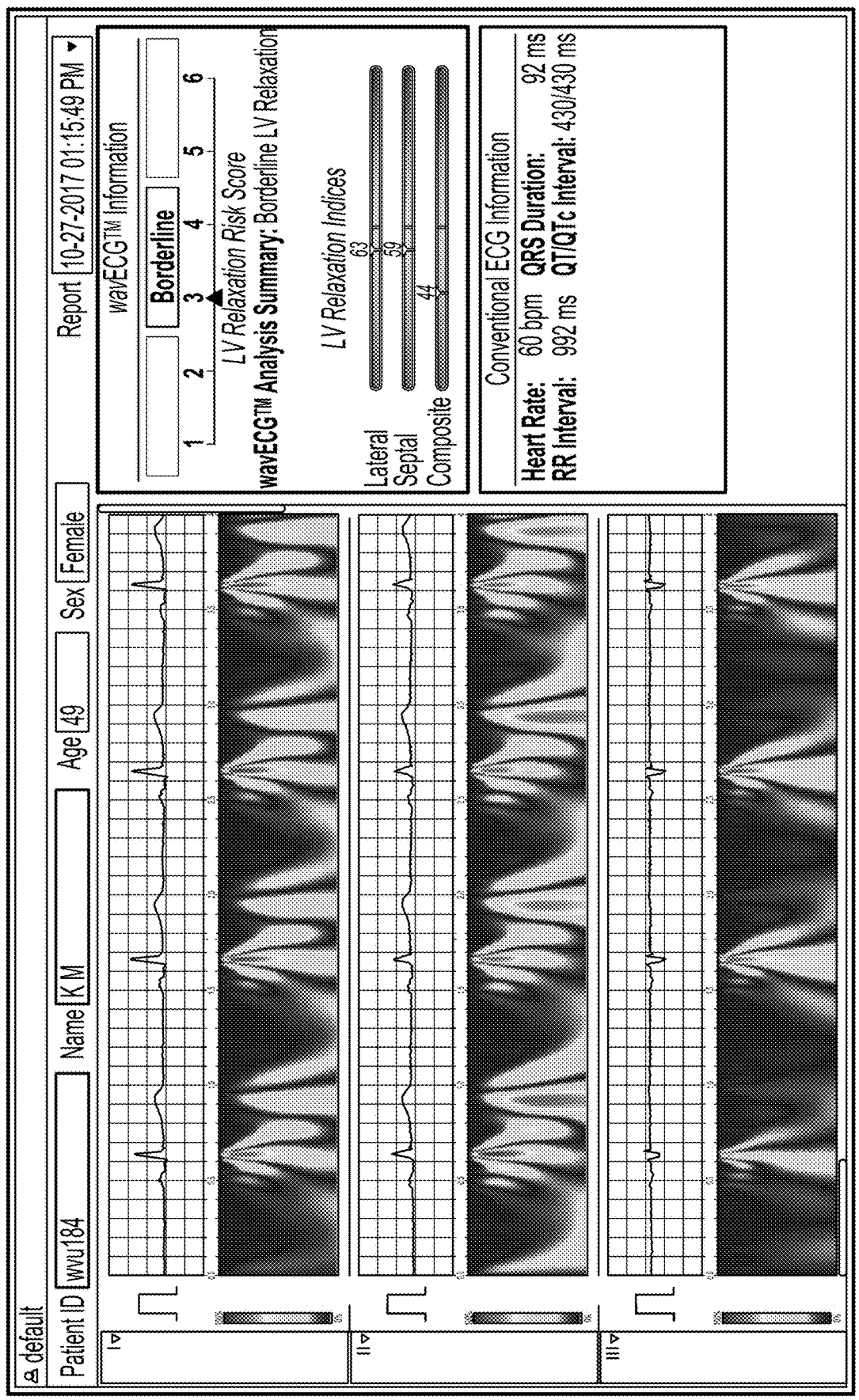
FIG. 8 is a user interface showing an example report screen for a borderline case in accordance with various embodiments.

FIGS. 7 and 8 are example user interfaces in accordance with various embodiments, e.g., as may be displayed on a computing device (e.g., desktop computer or tablet) utilized by a physician or other medical provider when evaluating a patient. The user interface in FIG. 7 shows an example report screen for an abnormal case, whereas the user interface in FIG. 8 shows an example report screen for a borderline case. The report screens display, on the left side, the ECG traces and associated time-frequency maps for multiple leads (e.g., as shown, leads I, II, and III). The displayed leads may be selectable (e.g., among the standard twelve leads) by the user (e.g., physician), using, for example, drop-down lists accessible via user-interface features next to the lead indicators. For the purpose of displaying the time-frequency maps to the user, the unsigned version may be beneficial since it avoids presenting potentially distracting information that is not of immediate, intuitively discernible clinical significance because the sign is not relevant to an intuitive interpretation of the signal value of the time-frequency map as a measure of the electrical energy of the heart.

On the right side of the example report screens, various quantitative and qualitative metrics and indicators are displayed. These metrics may include conventional ECG information, such as Glasgow parameters (e.g., heart rate, various intervals measured between waveform features of the ECG, etc.). In addition, various diastolic indicators derived, in accordance with this disclosure, by machine-learned computational models from ECGs and time-frequency maps may be shown. For instance, a categorical indicator, e.g., displayed in the form of a segmented bar (optionally color-coded) with the applicable category being highlighted and the other categories being greyed out, may instantly inform the physician of the overall diastolic health of the patient, e.g., whether diastolic function is normal, borderline (as in FIG. 8), or abnormal (as in FIG. 7). As will be appreciated, a five-segment bar may alternatively be used for finer gradation. Alternatively or additionally, a quantitative risk score, which generally correlates with the classification, may be indicated along a scale. For example, a high risk score of about 6 may correspond to an abnormality, whereas a lower risk score of about 3 may correspond to borderline diastolic function. A textual risk statement indicating the type and/or likelihood of abnormality may also be included. Further, to provide information familiar to physicians from echocardiograms, the report screen may also provide the computed echocardiogram parameter estimates, or indices derived therefrom, e.g., as shown, lateral, septal, and composite LV relaxation indices. Along with the numerical values, a graphical representation of likelihood ratios for the various indices may be provided (e.g., by tick-marks along a scale, as shown). As can be seen from a comparison of FIGS. 7 and 8, abnormal diastolic function may be reflected in significantly higher values of the LV relaxation indices. Other graphic, numerical, and/or textual representations are conceivable. In general, the displayed information includes various measures and indicators that may be useful for risk stratification.

To aid with the interpretation of the information displayed on the report screen (or made available by other means), medical personnel may also be provided with an interpretation guide that presents statistical measures taken from a reference study population. As an example, table 1 below illustrates the kind of more detailed information that the interpretation guide may contain to explain risk classifications (e.g., into normal/borderline/abnormal), risk scores, and verbal risk assessments.

TABLE 1

| Output Type | Output Value | Interpretation |
|---|---|---|
| Summary Classification | Abnormal | LVDD relative risk: 12.1<br>95% CI [4.68, 31.11] p <0.0001 |
| LV Relaxation Risk Score | 5 | Predicted average e' range:<br>70% CI [5.68, 9.09]<br>95% CI [3.97, 10.79] |
| Risk Statement | Probable Ischemic or Structural Abnormality | 84.5% observed with LVDD |

As another example, Table 2 provides various statistical measures for relating LV relaxation indices to normal/borderline/abnormal classifications:

TABLE 2

| LV Relaxation Index | Classification | Statistical measures |
|---|---|---|
| Lateral = 76 | Abnormal | Percentile (abnormal): 71%<br>Percentile (normal): 4%<br>Likelihood Ratio: 17.75 |
| Septal = 68 | Borderline | Percentile (abnormal): 45%<br>Percentile (normal): 8%<br>Likelihood Ratio: 5.63 |
| Composite = 66 | Borderline | Percentile (abnormal): 40%<br>Percentile (normal): 3%<br>Likelihood Ratio: 13.33 |

As can be seen from this data, within the reference study population, among patients with a diastolic abnormality, 71% have a lateral index of at least 76, but only 4% of patients with normal diastolic function reach a lateral index that high, for a high likelihood ratio of 17.75; accordingly, a lateral index of 76 results in a classification as abnormal. By contrast, for a septal index of 68, the corresponding fractions of patients in the reference study population with abnormal versus normal diastolic function that reach or exceed that index value are 45% and 8%, respectively, for a much lower likelihood ratio of 5.63; in this case, a classification as borderline results.

FIG. 9 is a block diagram of a machine in the example form of a computer system 900 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. While only a single machine is illustrated, the term "machine" shall also be taken to include any collection of machines that individually or jointly execute a set (or multiple sets) of instructions to perform any one or more of the methodologies discussed herein. The example computer system 900 includes one or more processors 902 (e.g., a central processing unit (CPU), a graphics processing unit (GPU) or both), a main memory 904 and a static memory 906, which communicate with each other via a bus 908. The computer system 900 may further include a video display unit 910 (e.g., a liquid crystal display (LCD) or a cathode ray tube (CRT)). The computer system 900 also includes an alphanumeric input device 912 (e.g., a keyboard), a user interface (UI) navigation device 914 (e.g., a mouse), a disk drive unit 916, a signal generation device 918 (e.g., a speaker), a network interface device 920 to communicate via a network 926, and a data interface device (such as, e.g., an electrode interface).

The disk drive unit 916 includes a machine-readable medium 922 storing one or more sets of instructions and data structures (e.g., software) 924 embodying or utilized by any one or more of the methodologies or functions described herein. The instructions 924 may also reside, completely or at least partially, within the main memory 904 and/or within the processor 902 during execution thereof by the computer system 900, the main memory 904 and the processor 902 also constituting machine-readable media.

While the machine-readable medium 922 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding, or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; CD-ROM and DVD-ROM disks, or other data-storage devices. Further, the term "machine-readable medium" shall be taken to include a non-tangible signal or transmission medium, including an electrical signal, a magnetic signal, an electromagnetic signal, an acoustic signal and an optical signal.

The following numbered examples are illustrative embodiments:

1. A method for quantifying diastolic function, the method comprising: receiving one or more electrocardiograms measured for a patient; converting the one or more electrocardiograms, using time-frequency transform, into time-frequency features; operating one or more machine-learned computational models on input comprising the time-frequency features to compute an estimate or estimates of one or more echocardiogram parameters indicative of diastolic function, the one or more machine-learned computational models having been trained in a supervised manner using values of the one or more echocardiogram parameters obtained by echocardiography as ground-truth outputs.

2. The method of example 1, further comprising computing one or more additional indicators of diastolic function based at least in part on the estimate or estimates of the one or more echocardiogram parameters.

3. The method of example 2, wherein the one or more additional indicators of diastolic function are computed by operating one or more second machine-learned computational models on input comprising the estimate or estimates of the one or more echocardiogram parameters.

4. The method of example 3, wherein the one or more second machine-learned computational models comprise one or more ensemble models.

5. The method of example 2 or example 3, wherein the one or more additional indicators of diastolic function comprise at least one of a left ventricular relaxation risk score, a lateral left ventricular relaxation index, a septal left ventricular relaxation index, or a composite left ventricular relaxation index.

6. The method of any of examples 2-5, wherein the one or more additional indicators of diastolic function comprise a categorical diastolic function indicator.

7. The method of example 6, wherein the categorical diastolic indicator has a value range comprising normal, abnormal, and borderline diastolic function.

8. The method of example 6, wherein the categorical diastolic indicator has a value range comprising low-possibility, possible, borderline, probable, and highly probable left ventricular relaxation abnormality.

9. The method of any of examples 6-8, wherein the categorical diastolic function indicator is determined by comparison of the estimate or estimates of the one or more echocardiogram parameters against one or more thresholds.

10. The method of any of examples 1-9, wherein the one or more machine-learned computational models result from training on pairs of input feature sets and a ground-truth outputs for a plurality of patients, the input feature sets comprising the time-frequency features.

11. The method of any of examples 1-9, wherein a first neural network is used to convert the electrocardiograms into the time-frequency features, wherein the one or more machine-learned computational models comprise one or more second neural networks, and wherein the time-frequency features output by the first neural network are provided as inputs to the one or more second neural networks.

12. The method of example 11, wherein weights of the first neural network are initialized to implement a time-frequency transform and are subsequently adjusted during end-to-end training of the combined first and second neural networks.

13. The method of example 12, wherein the one or more second neural networks are trained with fixed values of the weights of the first neural network prior to the end-to-end training of the combined first and second neural networks.

14. The method of any of examples 1-13, wherein the one or more computational models comprise one or more regression models.

15. The method of example 14, wherein the one or more regression models comprise at least one of a random forest model or a least squares model.

16. The method of any of examples 1-15, wherein the time-frequency features derived from the time-frequency maps comprise extrema across frequency at one or more points in time associated with the P, Q, R, S, or T waves.

17. The method of any of examples 1-16, wherein the input to the one or more computational models further comprises at least one of one or more patient demographic parameters or one or more time-domain features derived directly from the one or more electrocardiograms.

18. The method of example 17, wherein the one or more time-domain features derived directly from the electrocardiograms comprise Glasgow-derived parameters.

19. A system comprising: one or more hardware processors; and memory storing instructions which, when executed by the one or more hardware processors, perform operations comprising: receiving one or more electrocardiograms measured for a patient; converting the one or more electrocardiograms, using time-frequency transform, into time-frequency features; operating one or more machine-learned computational models on input comprising the time-frequency features to compute an estimate or estimates of one or more echocardiogram parameters indicative of diastolic function, the one or more machine-learned computational models having been trained in a supervised manner using values of the one or more echocardiogram parameters obtained by echocardiography as ground-truth outputs.

20. The system of example 19, the operations further implementing any of the operations or limitations of examples 2-18.

21. A non-transitory computer-readable medium storing processor-executable instructions which, when executed by one or more computer processors, cause the one or more computer processors to perform operations comprising: receiving one or more electrocardiograms measured for a patient; converting the one or more electrocardiograms, using time-frequency transform, into time-frequency features; operating one or more machine-learned computational models on input comprising the time-frequency features to compute an estimate or estimates of one or more echocardiogram parameters indicative of diastolic function, the one or more machine-learned computational models having been trained in a supervised manner using values of the one or more echocardiogram parameters obtained by echocardiography as ground-truth outputs.

22. The computer-readable medium of example 21, the operations further implementing any of the operations or limitations of examples 2-18.

Although the invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A method for quantifying heart function, the method comprising:
receiving one or more electrocardiograms measured for a patient;
operating, by one or more hardware processors, first-level machine-learned computational models on different subsets of a set of input features comprising features derived from the one or more electrocardiograms; and
operating, by one or more hardware processors, one or more second-level ensemble machine-learned computational models on input comprising outputs of the first-level machine-learned computational models to compute an estimate or estimates of one or more echocardiogram parameters indicative of heart function, the first-level and the one or more second-level ensemble machine-learned computational models having been trained in a supervised manner using values of the one or more echocardiogram parameters obtained by echocardiography as ground-truth outputs.

2. The method of claim 1, wherein the input features comprise time-domain features.

3. The method of claim 2, wherein the time-domain features comprise at least one Glasgow-derived parameters or features associated with any of P, Q, R, S, or T waves of the one or more electrocardiograms.

4. The method of claim 1, wherein the input features comprise time-frequency features derived from the one or more electrocardiograms.

5. The method of claim 4, wherein the time-frequency features are derived by discrete or continuous wavelet transform or short-time Fourier transform.

6. The method of claim 1, wherein the input features further comprise patient demographic parameters of the patient.

7. The method of claim 1, further comprising providing the estimate or estimates of the one or more echocardiogram parameters as output to clinical personnel.

8. The method of claim 1, further comprising computing one or more additional indicators of heart function.

9. The method of claim 8, further comprising providing the one or more additional indicators as output to clinical personnel.

10. The method of claim 8, wherein the one or more additional indicators are computed along with the estimate or estimates of the one or more echocardiogram parameters by the first-level and the one or more second-level ensemble machine-learned computational models.

11. The method of claim 8, wherein the one or more additional indicators are computed based at least in part on the estimate or estimates of the one or more echocardiogram parameters.

12. The method of claim 11, wherein the one or more additional indicators of heart function are computed by operating one or more additional machine-learned computational models on input comprising the estimate or estimates of the one or more echocardiogram parameters.

13. The method of claim 8, wherein the one or more additional indicators of heart function comprise one or more quantitative indicators.

14. The method of claim 13, wherein the one or more quantitative indicators comprises at least one of a left ventricular relaxation risk score, a lateral left ventricular relaxation index, or a septal left ventricular relaxation index.

15. The method of claim 8, wherein the one or more additional indicators of heart function comprise at least one categorical indicator.

16. The method of claim 15, wherein the at least one categorical indicator comprises an indicator with a value range comprising normal, abnormal, and borderline heart function.

17. The method of claim 1, wherein the one or more echocardiogram parameters comprise at least one of peak early diastolic mitral annular velocity (e'), peak late diastolic mitral annular velocity (a'), peak early diastolic transmitral flow velocity (E), peak late diastolic transmitral flow velocity (A), or ratios thereof.

18. The method of claim 1, wherein the first-level and the one or more second-level ensemble machine-learned computational models comprise a regression model.

19. A method for quantifying heart function, the method comprising:
receiving one or more electrocardiograms measured for a patient;
operating, by one or more hardware processors, a first neural network on the one or more electrocardiograms to perform a time-frequency transform; and
operating, by the one or more hardware processors, one or more second neural networks on input comprising output of the first neural network to compute an estimate or estimates of one or more echocardiogram parameters indicative of heart function, the one or more first and second neural networks having been trained in a supervised manner using values of the one or more echocardiogram parameters obtained by echocardiography as ground-truth outputs.

20. The method of claim 19, wherein the input to the one or more second neural networks further comprises the one or more electrocardiograms.

21. The method of claim 19, wherein one or more second neural networks comprise one or more initial network layers configured to derive or select at least one of time-domain features of the one or more electrocardiograms or time-frequency features from the output of the first neural network, and one or more subsequent network layers operating on the derived or selected time-domain or time-frequency features.

22. The method of claim 19, wherein the first neural network is a convolutional neural network.

23. The method of claim 19, wherein the first and second neural networks have been trained on training data comprising electrocardiograms labeled with respective values of the one or more echocardiogram parameters obtained by echocardiography.

24. The method of claim 23, wherein the first and second neural networks have been trained end-to-end.

25. The method of claim 23, wherein the first and second neural networks have been trained in two stages, the one or more second neural networks having been trained in a first stage with fixed weights of the first neural network, and the first and second neural networks having been trained in a subsequent second stage to adjust weights of both the first and second neural networks.

26. The method of claim 23, wherein, during training, weights of the first neural network have been initialized in accordance with the time-frequency transform.

27. The method of claim 19, wherein one or more second neural networks comprise one or more initial neural network layers configured to derive or select at least one of time-domain features or time-frequency features of the one or more electrocardiograms, and one or more subsequent network layers operating on the derived or selected time-domain or time-frequency features.

28. A system comprising:
one or more hardware processors; and
memory storing instructions which, when executed by the one or more hardware processors, perform operations comprising:
receiving one or more electrocardiograms measured for a patient;
operating first-level machine-learned computational models on different subsets of a set of input features comprising features derived from the one or more electrocardiograms; and
operating one or more second-level ensemble machine-learned computational models on input comprising outputs of the first-level machine-learned computational models to compute an estimate or estimates of one or more echocardiogram parameters indicative of heart function, the first-level and the one or more second-level ensemble machine-learned computational models having been trained in a supervised manner using values of the one or more echocardiogram parameters obtained by echocardiography as ground-truth outputs.

29. A non-transitory computer-readable medium storing processor-executable instructions which, when executed by one or more computer processors, cause the one or more computer processors to perform operations comprising:
receiving one or more electrocardiograms measured for a patient;
operating first-level machine-learned computational models on different subsets of a set of input features comprising features derived from the one or more electrocardiograms; and operating one or more second-level ensemble machine-learned computational models on input comprising outputs of the first-level machine-learned computational models to compute an estimate or estimates of one or more echocardiogram parameters indicative of heart function, the first-level and the one or more second-level ensemble machine-learned computational models having been trained in a supervised manner using values of the one or more echocardiogram parameters obtained by echocardiography as ground-truth outputs.

\* \* \* \* \*